United States Patent
Hoffman et al.

(10) Patent No.: US 6,241,984 B1
(45) Date of Patent: Jun. 5, 2001

(54) HUMAN HEMATOPOIETIC PROGENITOR CELL PREPARATIONS AND THEIR EXPANSION IN A LIQUID MEDIUM

(75) Inventors: Ronald Hoffman; John Brandt, both of Palo Alto, CA (US)

(73) Assignee: The Indiana University Foundation, Bloomington, IN (US)

( * ) Notice: Subject to any disclaimer, the term of this patent is extended or adjusted under 35 U.S.C. 154(b) by 0 days.

(21) Appl. No.: 08/226,513

(22) Filed: Mar. 31, 1994

Related U.S. Application Data

(63) Continuation-in-part of application No. 07/682,344, filed on Apr. 9, 1991, now abandoned.

(51) Int. Cl.$^7$ ................................................. C12N 5/08
(52) U.S. Cl. .................... 424/93.7; 424/93.1; 424/93.21
(58) Field of Search ........................... 435/240.1, 240.2, 435/2, 325; 424/85.2, 93.7, 93.21, 93.1; 604/4.5, 6, 48, 49; 514/2, 12

(56) References Cited

U.S. PATENT DOCUMENTS

| | | | |
|---|---|---|---|
| 5,061,620 | 10/1991 | Tsukamoto et al. | 435/7.21 |
| 5,087,570 | 2/1992 | Weissman et al. | 435/240.1 |
| 5,199,942 | * 4/1993 | Gillis | 604/4 |

OTHER PUBLICATIONS

W. Broxmeyer, et al. (1990) Exp. Hematology 18:615, A256. Enhanced biological activity of a human GM–CSF/IL–3 fusion protein.

M. Kobayahsi, et al. (1989) Blood 73:1836–1841. Interleukin–3 is significantly more effective than other colony stimulating factors in long term maintenance of human bone marrow derived colony forming cells in vitro.

I. McNiece, et al. (1991) Exp. Hematol. 19:226–231. Recombinant human stem cell factor synergises with GM–CSF, G–CSF, IL–3 and Epo to stimulate human progenitor cells of the myeloid and erythroid lineages.

J. Brandt, et al. (1990) J. Clin. Invest 86:932–941. Cytokine–dependent longterm culture of highly enriched precursors of hematopoietic progenitor cells from human bone marrow.

J. Brandt, et al. (1989) Blood 74(7) suppl. A420. In vitro characterization of human bone marrow cells with long term hematopoietic repopulating ability.

* cited by examiner

Primary Examiner—James Martinell

(57) ABSTRACT

A process for supporting hematopoietic progenitor cells in a culture medium which contains at least one cytokine effective for supporting the cells and preferably, is essentially free of stromal cells.

1 Claim, No Drawings

HUMAN HEMATOPOIETIC PROGENITOR CELL PREPARATIONS AND THEIR EXPANSION IN A LIQUID MEDIUM

This application is a continuation-in-part of U.S. patent application Ser. No. 07/682,344, filed Apr. 9, 1991, now abandoned.

TECHNICAL FIELD

The field of this invention is growth and expansion of hematopoietic cells in culture.

BACKGROUND

Mammalian hematopoiesis has been studied in vitro through the use of various long-term marrow culture systems. Dexter and co-workers described a murine system from which CFU-S and CFU-GM could be assayed for several months, with erythroid and megakaryocytic precursors appearing for a more limited time. Maintenance of these cultures was dependent on the formation of an adherent stromal cell layer composed of endothelial cells, adipocytes, reticular cells, and macrophages. These methods were soon adapted for the study of human bone manrow. Human long-term culture systems were reported to generate assayable hematopoietic progenitor cells for 8 or 9 wks and, later, for up to 20 wks. Such cultures are again relying on the preestablishment of a stromal cell layer which is frequently reinoculated with a large, heterogeneous population of marrow cells. Hematopoietic stem cells have been shown to home and adhere to this adherent cell multilayer before generating and releasing more committed progenitor cells. Stromal cells are thought to provide not only a physical matrix on which stem cells reside, but also to produce membrane-contact signals and/or hematopoietic growth factors necessary for stem cell proliferation and differentiation. This heterogeneous mixture of cells comprising the adherent cell layer presents an inherently complex system from which the isolation of discrete variables affecting stem cell growth has proven difficult.

Recently, a study was conducted by McNiece and Langley which examined the stimulatory effect of recombinant human stem cell factor (MGF) on human bone marrow cells alone and in combination with recombinant human colony stimulating factors, GM-CSF, IL-3 and erythropoietin. The results showed that MGF stimulation of low density non-adherent, antibody depleted CD34+ cells suggests that MGF directly stimulates progenitor cells capable of myek)id and erythroid differentiation.

RELEVANT LITERATURE

Conditions which allow long term in vitro bone marrow culture are described in Dexter, et al. (1977) J. Cell. Physiol. 91:335–344; Gartner, et al. (1980) P.N.A.S. 77:4756–4759 and Hocking, et al. (1980) Blood 56:118–124. Survival of granulocytic progenitors is shown by Slovick, et al. (1984) Exp. Hematol. 12:327–338. Roberts, et al. (1987) J. Cell. Physiol. 132:203–214 describes the use of 3T3 cells in such cultures.

Cell surface antigen expression in hematopoiesis is discussed in Strauss, et al. (1983) Blood 61:1222–1231 and Sieff, et al. (1982) Blood 60:703–713. Descriptions of pluripotential hematopoietic cells; are found in McNiece, et al. (1989) Blood 74:609–612 and Moore, et al. (1979) Blood Cells 5:297–311. Characterization of a human hematopoietic progenitor cell capable of forming blast cell containing colonies in vitro is found in Gordon, et al. (1987) J. Cell. Physiol. 130:150–156 and Brandt, et al. (1988) J. Clin. Invest. 82:1017–1027.

Characterization of stromal cells is found in Tsai, et al. (1986) Blood 67:1418–1426 and Li, et al. (1985) Nature 316:633–636. The localization of progenitor cells in the adherent layer of cultures is discussed in Coulombel, et al. (1983) Blood 62:291–297 and Gordon, et al. (1985) Exp. Hematol. 13:937–940.

Eliason, et al. (1988) Exp. Hematol. 16:307–312 describes GM-CSF and IL-3 in hematopoiesis. The effect of growth factors in megakaryopoiesis is found in Brno, et al. (1988) Exp. Hematol. 16:371–377. McNiece, et al (1991) Exp. Hematol. 19:226–231 describes the use of stem cell factor in in vitro cultures.

SUMMARY OF THE INVENTION

In accordance with an aspect of the present invention there is provided a process for supporting mammalian bone marrow cells wherein such cells are maintained in a culture medium essentially free of stromal cells and which includes at least one cytokine effective for supporting such cells.

DESCRIPTION OF THE SPECIFIC EMBODIMENTS

Preferred embodiments of this aspect of the present invention provide a process for supporting bone marrow cells which are hematopoietic stem cells, a process for supporting bone marrow cells which are hematopoietic progenitor cells and a process for supporting bone marrow cells which are CD34+ DR− CD15− cells.

In addition this invention provides that at least one cytokine be selected from the following cytokines: Interleukin (IL)-1, IL-3, IL-6, granulocyte/macrophage-colony stimulating factor (GM-CSF), human or murine stem cell factor, sometime referred to as human or murine mast cell growth factor (MGF) or Steel Factor (SL) and a fusion protein of GM-CSF/IL-3 (FP).

In accordance with another aspect of the present invention there is provided a process for supporting mammalian bone marrow cells wherein such cells are maintained in a culture medium containing a combination of cytokines effective for supporting such cells. Preferably, the bone marrow will be supported in a culture medium which is essentially free of stromal cells.

Additional preferred embodiments of this invention provide a process for supporting bone marrow cells which are he-matopoietic stem cells. A process for supporting bone marrow cells which are hematopoietic progenitor cells and a process for supporting bone marrow cells which are CD34+ DIR− CD15− cells.

Preferably, the culture medium will contain at least one of the following cytokine combinations IL-1/IL-3; IL-3/IL,-6; IL-3/MGF; IL-3/GM-CSF; MGF/FP. Applicant has found that such combinations provide for an improved rapid expansion of the cell population.

The term "supporting" with respect to stem cells and other progenitor cells means maintaining and/or expanding and/or promoting some differentiation of such cells.

The following are representative examples of cytokines which may be employed in the present invention. The cytokines may be human in origin, or may be derived from other mammalian species when active- on human cells. IL-1 is used in an amount effective to support the cells, generally such amount is at least 1 U/ml and need not exceed 10 U/ml, preferably 2.5 U/ml, where the specific activity is $10^8$ CFU/mg protein. IL-6 is used in an amount effective to support the cells, generally such amount is at least 500 pg/ml and need not exceed 10 ng/ml, preferably 1 ng/ml. IL-3 is used in an amount effective to support the cells, generally such amount is at least 500 pg/ml and need not exceed 2 ng/ml, preferably 500 pg/ml. GM-CSF is used in an amount effective to support the cells, generally such amount is at least 100 pg/ml and need not exceed 1 ng/ml, preferably 200 pg/ml. c-kit ligand (MGF, steel factor, stem cell factor) may be human or murine in origin, is used in an amount effective to support the cells, generally such amount is at least 10 ng/ml and need not exceed 500 ng/ml, preferably 50 to 100 ng/ml. FP (fusion protein of IL-3 and GM-CSF as described in Broxmeyer, et al. [1990] Exp. Hematol. 18:615) is used in an amount effective to support the cells, generally such amount is at least 1 ng/ml and need not exceed 25 ng/ml, preferably 10 ng/ml.

The use of a cytokine in. the absence of stromal cells is particularly suitable for expanding the mammalian bone marrow stem cells and in particular progenitor cells. The cells which are supported in accordance with the present invention are preferably of human origin.

In accordance with a preferred aspect of the present invention, a cell population which is supported in accordance with the present invention is that which is positive for CD34 antigen and is negative for HLA-DR and is also negative for CD15.

Specifically this aspect of the present invention provides for a cell population of CD34+ DR− CD15− supported in accordance with the process described above, where the population has doubled in a period of time which does not exceed 15 days. Preferably, the population has doubled in 7 to 15 days.

In accordance with another aspect, the present invention provides for a cell population of bone marrow cells supported in accordance with the process described herein, where the population has doubled in a period of time which does not exceed 15 days. Preferably, the population has doubled in 7 to 15 days.

In accordance with another aspect, the present invention provides for a cell population of hematopoietic progenitor cells supported in accordance with the process described herein, where the population has doubled in a period of time which does not exceed 15 days. Preferably, the population has doubled in 7 to 15 days.

In accordance with another aspect, the present invention provides for a cell population of hematopoietic progenitor cells supported in accordance with the process described herein, where the population has doubled in a period of time which does not exceed 15 days. Preferably, the population has doubled in 7 to 15 days.

Another aspect of the present invention provides for a composition comprised of an expanded bone marrow cell culture which is essentially free of stromal cells, the culture also contains at least one cytokine and the culture's cell population has doubled in a time not exceeding 15 days. Preferably, the cell population will have doubled in at least 7 and not exceeding 15 days.

An additional aspect of the present invention provides for a composition comprised of an expanded bone marrow cell culture which contains a combination of cytokines and the cultures cell population has doubled in a time not to exceed 15 days. Preferably, the cell population has doubled in at least 7 and not exceeding 15 days. It is also preferable, that the cell culture be essentially free of stromal cells.

As previously indicated, the present invention is particularly applicable to marrow cells that are positive for CD34 antigen but which do not express HLA-DR, CD15 antigens in that it is believed that such c(ell population is believed to be closely associated with human hematopoietic stem cells, but it is to be understood that the present invention is not limited to supporting such a cell population.

The cells supported in accordance with the present invention may be used in a variety of ways. For example, such cells may be employed as part of a bone marrow transfer procedure.

Expanded hematopoietic stem cell populations can be used as grafts for hematopoietic cell transplantation. Autologots transplantation may be used to treat malignancies, while heterologous transplantation may be used to treat bone marrow failure states and congenital metabolic, immunologic and hematological disorders. Marrow samples will be taken from patients with cancer prior to cytoreductive therapy, and CD34+ DR− CD15− cells isolated by means of density centrifugation, counterflow centrifugal elutriation, monoclonal antibody labelling and fluorescence activated cell sorting. The stem cells in this cell population will then be expanded ex vivo and will serve as a graft for autologous marrow transplantation. The cells will be expanded in accordance with the methods of the subject invention, culturing the cells with a combination of growth factors as described. The cellular preparation will be administered to the patient following curative cytoreductive therapy e.g. chemoradiotherapy.

Expanded stem cell populations an also be utilized for in utero transplantation during the first trimester of pregnancy. Fetuses with metabolic and hematologic disorders will be diagnosed prenatally. Marrow will be obtained from normal individuals and CD+ DR− CD15− cells will be obtained by the methods described previously and expanded in vitro. They will then be administered to the fetus by in utero injection. A chimera will be formed which will lead to partial but clinically significant alleviation of the clinical abnormality.

The invention will be further described with respect to the following examples; however, the scope of the invention is not to be limited thereby.

The following examples are offered by way of illustration and not by way of limitation.

EXPERIMENTAL

Example 1

A. Materials and Procedures

Prior to performing any procedures, informed consent was obtained from all volunteers according to the guidelines of the Human Investigation Committee of the Indiana University School of Medicine.

Cell separation techniques. Bone marrow aspirates were collected from the posterior iliac crests of normal volunteers. Low-density mononuclear bone marrow (LDBM) cells were obtained by density centrifugation of the heparinized marrow over Ficoll-Hypaque (Pharmacia Fine Chemicals, Piscataway, N.J.) at 500 g for 25 min. LDBM cells were suspended in PBS-EDTA (PBTS, pH 7.4, containing 5% FBS, 0.01% EDTA wt/vol, and 1.0 g/liter D-glucose) and injected into an elutriator system at 10° C. at a rotor speed of 1,950 rpm using a JA-17 rotor and standard separation chamber (Beckman Instruments, Inc., Palo Alto, Calif.). A fraction of the LDBM eluted at a flow rate of 12–14 ml/min (FR 12–14), enriched for hematopoietic precursors, was collected as described in Brandt, et al. (1988) J. Clin. Invest 82:1017–1027.

Long-term marrow cultures free of stromal cells. Plastic 35-mm tissue culture dishes were seeded with $2\times10^6$ LDBM cells in 1 ml of Iscove's with 10% FBS and $2\times10^{-5}$ M methylprednisolone. Cultures were incubated at 37° C. in 100% humidified atmosphere containing 5% $CO_2$ in air and fed weekly by total replacement of media. Stromal cells were confluent by 4–6 wk. The stromal cultures were then irradiated with 1,500 rad, the media were replaced, and the cultures were inoculated with $5\times10^3$ sorted bone marrow cells from autologous donors. The media in these cultures were removed at 7–10 d intervals and replaced with fresh media. Suspended, nonadherent cells were then counted and assayed for progenitors.

Long-term suspension cultures. Plastic 35-mm tissue culture dishes containing 1 ml of Iscove's with 10% FBS were inoculated with stromal cell free long-term marrow cells containing $5\times10^3$ cells obtained by sorting and incubated at 37° C. in 100% humidified atmosphere containing 5% $CO_2$ in air. At this time, and every 48 h thereafter, cultures received nothing (1% BSA/PBS), 2.5 U/ml IL-1α, 50 U/ml IL-3, 75 U/ml IL-6, 12.5 U/ml GM-CSF, or combinations of the above. At 7 d intervals, cultures were demi-depopulated by removal of one-half the culture volume which was replaced with fresh media. Cells in the harvested media were counted, transferred to slides for staining and morphological examination, and assayed for various progenitor cells.

Hematopoietic growth factors. All cytokines were obtained from the Genzyme Corp., Boston, Mass. Recombinant IL-1α and IL-3 each had a specific activity of $10^8$ CFU/mg protein, while that of IL-6 was $10^7$ and granulocyte/macrophage colony-stimulating factor (GM-CSF) $5\times10^7$ CFCc/mg protein.

Two- and three-color cell sorting. FR 12–14 cells were incubated with mouse monoclonal anti-HPCA-1 ((CD34) of the $IgG_1$ subclass (Becton Dickinson Immunocytometry Systems, San Jose, Calif.), washed, and stained with Texas red-conjugated, subclass-specific goat anti-mouse $IgG_1$ (Southern Biotechnology Associates, Inc., Birmingham, Ala.). Cells were next incubated with mouse serum to block any unbound active sites on the second-step antibody. Cells were finally stained with phycoerythrin-conjugated mouse anti-HLA-DR either alone or in combination with FITC-conjugated CD33 (My9, Coulter Immunology, Hialeah, Fla.), CD15 (Leu-M1), or CD71 (transferrin receptor) (Becton Dickinson Immunocytometry Systems). CD15 is present on cells of the granulocytic and monocytic lineages, and an anti-CD15 monoclonal antibody was employed in the hope of eliminating these cellular components from the cell populations (Strauss, et al. [1983] Blood 61:1222–1231). CD71 is present on actively proliferating cells and an anti-CD71 antibody was utilized to separate actively proliferating cells from more quiescent marrow elements (Sieff, et al. [1982] Blood 60:703–713). Controls consisted of the corresponding isotype-matched, nonspecific myeloma proteins used in parallel with staining monoclonal antibodies. Cells were stained at a concentration of $2\times10^7$/ml and washed after each step in 1% BSA in PBS. A temperature of 4° C. was maintained throughout the procedure.

Immediately after staining;, cells were sorted on a Coulter Epics 753 dual-laser flow cytometry system (Coulter Electronics, Inc., Hialeah, Fla.). Texas Red was excited by 590 nm light emitted from a rhodamine 6G dye laser. FITC and phycoerythrin were excited using the 488 nm wavelength from a dedicated 6-W argon laser. Sorting windows were first established for forward angle light scatter (FALS) and Texas red fluorescence. Positivity for each fluorochrome was defined as fluorescence >99% of that of the controls. Cells were next gated on the presence or absence of detectable HLA-DR-phycoerythrin and CD33-FITC, CD15-FITC, or CD71-FITC.

Hematopoietic progenitor cells assays. Cells were suspended at various concentrations in 35-mm plastic tissue culture dishes (Costar Data Packaging, Cambridge, Mass.) containing 1 ml of 30% FBS, $5\times10^{-5}$ M 2-mercaptoethanol, 1 U human purified erythropoietin (50 U/mg protein, Toyobo Co. Ltd., Osaka, Japan), 50 U GM-CSF, and 1.1% methylcellulose in Iscove's modified Dulbecco's medium. The cultures were incubated at 37° C. in a 100% humidified atmosphere containing 5% $CO_2$ in air. After 14 d, erythropoietic bursts (BFU-E), granulocyte-macrophage (CFU-GM), and mixed lineage (CFU-GEMM) colonies were scored in situ on an inverted microscope using standard criteria for their identification (Brandt, supra).

High proliferative potential colony-forming cell (HPP-CFC)-derived colonies were enumerated after 28 d in culture according to the recently published criteria of McNiece and co-workers. The human HPP-CFC-derived colony is a late-appearing, very large (0.5 mm or more in diameter) colony composed primarily of granulocytes with a lesser number of monocytes; cell numbers frequently exceed 50,000.

Cells removed from suspension cultures were assayed for CFU-megakaryocyte (CFU-MK) colonies using the serum-depleted method described in detail by Bruno et al. (1988) Exp. Hematol 16:371–377. $5\times10^3$ cells per point were suspended in a 1-ml serum-substituted fibrin clot with 100 U of IL-3 in 35-mm culture dishes and incubated at 37° C. in a 100% humidified atmosphere containing 5% $CO_2$ in air. At 18–24 d, cultures were fixed in situ and stained using rabbit anti-human platelet glycoprotein antisera, and fluorescein-conjugated goat $F(ab')_2$-specific anti-rabbit IgG (Tago, Inc., Burlingame, Calif.) and megakaryocyte colonies were enumerated on a Zeiss fluorescence microscope (Carl Zeiss, Inc., New York, N.Y.). A positive colony was defined as a cluster of three or more fluorescent cells.

B. Experiments

A liquid culture system supplemented with repeated 48-hourly cytokine additions was utilized to study cell populations. Total cell production by both $CD34^+DR^-CD15^-$ and $CD34^+DR^-CD71^-$ cells is shown in Tables I and II while assayable CFU-GM in these cultures over time are recorded in Tables III and IV. In the absence of exogenous cytokines, total cell numbers declined over a 2-week period and assayable CFU-GM persisted for only 1 or 2 wk. The repeated addition of IL-1α did not significantly enhance total cell production or generation of CFU-GM by either CD34+DR−CD15− or CD34+DR-CD71− cells. IL-6 did not alter total cell numbers or number of assayable CFU-GM in cultures initiated with $CD34^+DR^-CD71^-$ cells. By contrast, IL-6 increased total cell numbers over seven fold by week 3 by $CD34^+DR^-CD15^-$ initiated cultures but did not appreciably extend the interval over which CFU-GM were detected. In both sets of experiments, GM-CSF promoted increased total cell production for 6 wk, by which time cell numbers represented 20–80 times the number present in the initial seeding populations. Assayable CFUJ-GM persisted for 3–4 weeks and cumulatively surpassed those assayable in the initial populations. The single most effective cytokine in terms of promoting cellular expansion, increasing the number of CFU-GM, and lengthening the duration of time over which CFU-GM were assayable was IL-3. Both $CD34^+DR^-CD15^-$ and $CD34^+DR^-CD71^-$ cells experienced 200-fold increases in cell numbers by day 28, and, after 1 or 2 weeks in culture, contained equal or slightly greater numbers of CFU-GM than present in the initial inoculi. Assayable progenitors were produced for 4–5 weeks in the system when maintained with IL-3, and viable cell counts remained high at 8 wk. IL-1α or IL-6 prolonged and enhanced these effects when added in combination with IL-3. CFU-GM were assayable after 8 weeks in suspension culture after continued treatment with these two cytokine combinations. No adherent cell layer was established in any of the suspension cultures over the 8-week period of observation.

In a separate experiment, $CD34+DR^-CD71^-$ cells were grown in this suspension culture system in the presence of a combination of both IL-3 and IL-6 and assayed for CFU-MK from days 7 through 28 of culture. CFU-MK were detected over this 28 d period (Table V). Utilizing this IL-3/IL-6 cytokine combination, the ability of $CD34^+DR^-CD15^+$ and $CD34^+DR^-CD71^+$ cells to sustain long-term hematopoiesis was compared to that of the $CD34^+DR^-CD15^-$ and $CD34^+DR^-CD71^-$ fractions (Table VI). Both the CD15-positive and CD71-positive cells failed to generate CFU-GM after 2 wk, and the CD71-positive population, which initially included the overwhelming majority of BFU-E, failed to produce assayable BFU-E after only 7 d in culture.

Morphological analysis of the cells in these suspension cultures during the period of observation revealed changes in the cellular composition of the populations following the addition of various cytokines (Tables VII and VIII). IL-1α- and IL-6-containing cultures behaved very similarly to the control samples. Cultures to which no cytokines were added were composed of 90–100% blasts after 1 wk; the CD34$^+$ DR$^-$CD15$^-$ cells did not survive 2 weeks in the absence of cytokine whereas the CD34$^+$DR$^-$CD71$^-$ initiated cultures were composed of 40% blasts and 60% monocytes by week 2. Cultures receiving IL-1α had a similar cellular composition. IL-6 facilitated some differentiation to the granulocytic series by both cell populations; the CD34+DR$^-$CD15$^-$ cells produced a significant number of mature granulocytic elements by week 2. GM-CSF, as well as IL-3, reduced the percentage of blasts in these suspension cultures appreciably by day 7. GM-CSF-containing cultures of CD34$^+$DR$^-$CD15$^-$ and CD34$^+$DR$^-$CD71$^-$ cells consisted primarily of metamyelocytes through 4 wk, with a shift to monocytes occurring by week 6.

IL-3 was unique in that, at 3 wk, suspension cultures initiated by either CD34$^+$DR$^-$CD15$^-$ or CD34$^+$DR$^-$CD71$^-$ cells were composed of 48% basophils in the presence of this growth factor (Tables VII and VIII). Addition of IL-1α or IL-6 did not alter this trend, all IL-3-containing cultures beirng composed of about 50% basophils by 3 weeks and retaining significant numbers of basophils throughout the duration of culture.

The cellular composition of hematopoietic colonies assayed from aliquots of the suspension cultures was comparable to th(ose assayed form the original sorted populations with a few notable exceptions. Blast cell colonies, as well as HPP-CFC-derived colonies, were routinely obtained by directly assaying CD34$^+$DR$^-$CD15$^-$ or CD34$^+$DR$^-$CD71$^-$ cells while these colony types were not observed in subsequent clonal assays of cellular aliquots obtained from the long-term liquid cultures. Distribution of GM colony subtypes, however, remained fairly consistent with roughly 40% being granulocyte macrophage, 40% monocyte macrophage, and 20% basophil or eosinophil colonies in either assays initiated with sorted cells of those initiated on days 7 through 42 of liquid culture. These CFU-GM-derived colonies ranged in size from 100 to 2,000 cells with the average colony containing between 200 to 400 cells. After 8 weeks of suspension culture, monocyte macrophage colonies were the predominant colony type observed in the clonal assays.

TABLE I

Total Cell Production of CD34+, DR$^-$, CD15$^-$ Cells after Addition of Various Cytokines

| Cytokine | Day | | | | | | | |
|---|---|---|---|---|---|---|---|---|
| | 0 | 7 | 14 | 21 | 28 | 35 | 42 | 56 |
| | | | | viable cell count × 10$^3$ | | | | |
| None | 5 | 1 | 4 | 0 | 0 | 0 | 0 | 0 |
| IL-1* | 5 | 2 | 2 | 0 | 0 | 0 | 0 | 0 |
| IL-3$^+$ | 5 | 53 | 140 | 591 | 1,085 | 533 | 678 | 781 |
| IL-6§ | 5 | 3 | 4 | 36 | 26 | 16 | 0 | 0 |
| GM-CSF° | 5 | 8 | 14 | 44 | 169 | 213 | 118 | 0 |
| IL-1α/IL-3 | 5 | 32 | 167 | 556 | 1,360 | 1,387 | 758 | 1,069 |
| IL-6/IL-3 | 5 | 47 | 171 | 471 | 854 | 1,440 | 1,200 | 1,216 |

Total cells = cells/ml cultured (1/2)n, where n = number of previous demi-depopulations.
*2.5 U/ml recombinant human IL-1α were added every 48 h; specific activity 10$^8$ CFU/mg protein.
+ 50 U/ml recombinant human IL-3 were added every 48 h; specific activity 10$^8$ CFU/mg protein.
§75 U/ml recombinant human IL-6 were added every 48 h; specific activity 10$^7$ CFU/mg protein.
°12.5 U/ml recombinant human GM-CSF were added every 48 h; specific activity 5 × 10$^7$ CFU/mg protein.

TABLE II

Total Cell production of CD34$^+$, DR$^-$, CD71$^-$ Cells after Addition of Various Cytokines

| Cytokine | Day | | | | | | | |
|---|---|---|---|---|---|---|---|---|
| | 0 | 7 | 14 | 21 | 28 | 35 | 42 | 56 |
| | | | | viable cell count × 10$^3$ | | | | |
| None | 5 | 1 | 2 | 0 | 0 | 0 | 0 | 0 |
| IL-1* | 5 | 3 | 0 | 0 | 0 | 0 | 0 | 0 |
| IL-3$^+$ | 5 | 40 | 226 | 964 | 746 | 1,190 | 1,120 | 851 |
| IL-6§ | 5 | 1 | 2 | 0 | 0 | 0 | 0 | 0 |
| GM-CSF° | 5 | 3 | 34 | 44 | 45 | 445 | 438 | 0 |
| IL-1α/IL-3 | 5 | 23 | 202 | 684 | 1,112 | 835 | 800 | 1,067 |

Total cells = cells/ml cultured (1/2)n, where n = number of previous demi-depopulations.
*2.5 U/ml recombinant human IL-1α were added every 48 h; specific activity 10$^8$ CFU/mg protein.
$^+$50 U/ml recombinant human IL-3 were added every 48 h; specific activity 10$^8$ CFU/mg protein.
§75 U/ml recombinant human IL-6 were added every 48 h; specific activity 10$^7$ CFU/mg protein.
°12.5 U/ml recombinant human GM-CSF were added every 48 h; specific activity 5 × 10$^7$ CFU/mg protein.

TABLE III

Total CFU-GM Production by CD34+, DR−, CD15− Cells after Addition of Various Cytokines

| Cytokine | Week |  |  |  |  |  |  |
|---|---|---|---|---|---|---|---|
|  | 1 | 2 | 3 | 4 | 5 | 6 | 7 |
|  | CFU-GM/ml culture |  |  |  |  |  |  |
| None | 40 | 0 | 0 | 0 | 0 | 0 | 0 |
| IL#1* | 22 | 14 | 0 | 0 | 0 | 0 | 0 |
| IL-3+ | 432 | 696 | 591 | 325 | 0 | 0 | 0 |
| IL-6§ | 42 | 242 | 96 | 0 | 0 | 0 | 0 |
| GM-CSF° | 273 | 200 | 219 | 0 | 0 | 0 | 0 |
| IL-1α/IL-3 | 254 | 397 | 444 | 408 | 139 | 152 | 64 |
| IL-6/IL-3 | 98 | 342 | 236 | 768 | 864 | 1,080 | 384 |

Total CFU-GM = CFU-GM/ml culture (1/2)n, where n = number of previous demi-depopulations.
Cells were seeded at $5 \times 10^3$/ml. CFU-GM in initial (day 0) population = $555/5 \times 10^3$ cells. Colonies grown in methylcellulose containing 50 U/ml GM-CSF and enumerated after 14 d.
*2.5 U/ml recombinant human IL-1α were added every 48 h; specific activity $10^8$ CFU/mg protein.
+50 U/ml recombinant human IL-3 were added every 48 h; specific activity $10^8$ CFU/mg protein.
§75 U/ml recombinant human IL-6 were added every 48 h; specific activity $10^8$ CFU/mg protein.
°12.5 U/ml recombinant human GM-CSF were added every 48 h; specific activity $5 \times 10^7$ CFU/mg protein.

TABLE IV

Total CFU-GM Production by CD34+, DR−, CD71− Cells after Addition of Various Cytokines

| Cytokine | Week |  |  |  |  |  |  |
|---|---|---|---|---|---|---|---|
|  | 1 | 2 | 3 | 4 | 5 | 6 | 7 |
|  | CFU-GM/ml culture |  |  |  |  |  |  |
| None | 15 | 4 | 0 | 0 | 0 | 0 | 0 |
| IL-1a* | 20 | 0 | 0 | 0 | 0 | 0 | 0 |
| IL-3+ | 664 | 272 | 96 | 448 | 119 | 0 | 0 |
| IL-6§ | 51 | 14 | 0 | 0 | 0 | 0 | 0 |
| GM-CSF° | 402 | 360 | 135 | 28 | 0 | 0 | 0 |
| IL-1/IL-3 | 347 | 324 | 342 | 334 | 167 | 240 | 214 |

Total CFU-GM = CFU-GM/ml culture (1/2)n, where n = number of previous demi-depopulations.
Cells were seeded at $5 \times 10^3$/ml. CFU-GM in initial (day 0) population = $690/5 \times 10^3$ cells. Colonies grown in methylcellulose containing 50 U/ml GM-CSF and enumerated after 14 d.
*2.5 U/ml recombinant human IL-1a were added every 48 h; specific activity $10^8$ CFU/mg protein.
+50 U/ml recombinant human IL-3 were added every 48 h; specific activity $10^8$ CFU/mg protein.
§75 U/ml recombinant human IL-6 were added every 48 h; specific activity $10^7$ CFU/mg protein.
°12.5 U/ml recombinant human GM-CSF were added every 48 h; specific activity $5 \times 10^7$ CFU/mg protein.

TABLE V

Assayable CFU-MK in Long-Term Suspension Cultures of CD34+DR−CD71− Cells Receiving a Combination of IL-3 and IL-6

| Days in culture* | CFU-MK/ml culture+ |
|---|---|
| 7 | 42.6 ± 7.6§ |
| 14 | 67.6 ± 56.6 |
| 21 | 17.0 ± 11.8 |
| 28 | 20.2 ± 10.4 |

50 U/ml recombinant human IL-3 were added every 48 h; specific activity $10^8$ CFUc/mg protein. 75 U/ml recombinant human IL-6 were added every 48 h; specific activity $10^7$ CFU/mg protein.
*Cultures were demi-depopulated every 7 d.
+CFU-MK were assayed in serum-free fibrin clot culture containing 100 U/ml IL-3 colonies enumerated at days 18–24 of culture.
§Each point represents the mean ± SD of triplicate assays. Values are not corrected for the effects of demi-depopulated.

TABLE VI

Total CFU-GM and BFU-E Production by Sorted Cell Populations Stimulated with a Combination of IL-3 and IL-6

| Population | Week |  |  |  |  |  |
|---|---|---|---|---|---|---|
|  | 1 | 2 | 3 | 4 | 6 | 8 |
|  | CFU-GM (BFU-E)ml culture |  |  |  |  |  |
| CD34+DR−CD15− | 275 (10) | 286 (4) | 64 | 32 | 75 | 0 |
| CD34+DR−CD15+ | 7 (1) | 26 | 0 | 0 | 0 | 0 |
| CD34+DR−CD71− | 220 (5) | 330 (4) | 132 | 18 | 43 | 0 |
| CD34+DR−CD71+ | 13 | 16 | 0 | 0 | 0 | 0 |

Total CFU = CFU/ml culture/(1/2)n = number of previous demi-depopulations.
Cells were seeded at $5 \times 10^3$/ml. 50 U/ml recombinant human IL-3, specific activity $10^8$ CFU/mg protein and 75 U/ml recombinant human IL-6, specific activity $10^7$. CFU/mg protein were added every 48 h. Cells were seeded at $5 \times 10^3$/ml.

TABLE VII

Differential Analysis of CD34+, DR−, CD15− Cells after Addition of Various Cytokines

| Cytokine | Day | Blasts | Pro | Myelo | MM | Band % | Seg | Eo | Baso | E | Mo |
|---|---|---|---|---|---|---|---|---|---|---|---|
| Control | 7 | 100 |  |  |  |  |  |  |  |  |  |
| IL-1a* | 7 | 100 |  |  |  |  |  |  |  |  |  |
|  | 14 | 78 |  |  |  |  |  |  |  |  | 22 |
| IL-6+ | 7 | 100 |  |  |  |  |  |  |  |  |  |
|  | 14 | 27 | 11 |  | 9 |  | 13 | 38 |  |  | 2 |
|  | 21 | 9 |  |  | 48 | 2 | 7 |  | 17 |  | 17 |
|  | 28 |  |  |  | 30 |  | 4 |  |  |  | 66 |

TABLE VII-continued

Differential Analysis of CD34+, DR−, CD15− Cells after Addition of Various Cytokines

| Cytokine | Day | Blasts | Pro | Myelo | MM | Band % | Seg | Eo | Baso | E | Mo |
|---|---|---|---|---|---|---|---|---|---|---|---|
| GM-CSF§ | 7 | 25 | 24 |  | 27 | 3 | 21 |  |  |  |  |
|  | 14 | 9 | 1 |  | 46 | 3 | 21 |  | 13 |  | 7 |
|  | 21 | 3 | 2 | 1 | 62 | 3 | 5 |  | 22 |  | 2 |
|  | 28 | 6 |  | 1 | 43 | 7 | 3 |  | 6 | 2 | 32 |
|  | 35 |  |  |  | 4 |  |  |  |  |  | 96 |
|  | 42 |  |  |  | 1 |  |  |  |  |  | 99 |
| IL-3° | 7 | 21 | 44 |  | 35 |  |  |  | 1 |  |  |
|  | 14 | 7 | 7 |  | 53 |  |  |  | 33 |  |  |
|  | 21 | 8 |  |  | 44 |  |  |  | 48 |  |  |
|  | 28 | 5 |  |  | 35 | 3 | 9 |  | 35 |  | 13 |
|  | 35 | 2 |  |  | 16 | 5 | 20 |  | 25 |  | 32 |
|  | 42 |  |  |  | 15 |  | 2 |  | 20 |  | 63 |
| IL-1α/ IL-3 | 7 | 1 | 5 | 1 | 53 | 12 | 14 |  | 14 |  |  |
|  | 14 | 5 |  |  | 34 | 9 |  | 52 |  |  |  |
|  | 21 | 1 |  |  | 53 | 4 | 3 | 31 |  | 8 |  |
|  | 28 | 1 |  |  | 42 | 12 | 5 | 32 |  | 8 |  |
|  | 35 |  |  |  | 20 |  |  | 27 |  | 53 |  |
|  | 42 |  |  |  | 8 |  |  | 8 |  | 84 |  |
|  | 56 |  |  |  |  |  |  | 11 |  | 89 |  |
| IL-6/IL-3 | 7 | 19 | 26 | 2 | 40 | 5 | 4 |  | 4 |  |  |
|  | 14 | 2 | 2 |  | 46 | 3 | 1 |  | 46 |  |  |
|  | 21 | 5 | 1 |  | 37 | 1 | 7 |  | 48 |  | 1 |
|  | 28 | 4 | 1 |  | 37 | 10 | 8 |  | 35 |  | 5 |
|  | 42 | 1 |  |  | 8 |  | 1 |  | 9 |  | 81 |
|  | 56 |  |  |  | 2 |  |  |  | 3 |  | 95 |

Differential cell counts were performed on Wright-Giemsa stained cytocentrifuge preparations of cells removed from liquid culture. 200 cells per sample were classified; if < 200 cells appeared on a slide, all were classified.
Abbreviations:
Pro, promyelocytes;
Myelo, myelocytes;
MM, metamyelocytes;
Band, neutrophil band form;
Seg, segmented neutrophils;
Eo, eosinophils;
Baso, basophils;
E, erythrocytes; and
Mo, monocytes.
*2.5 U/ml recombinant human IL-1a were added every 48 h; specific activity $10^8$ CFU/mg protein.
+50 U/ml recombinant human IL-3 were added every 48 h; specific activity $10^8$ CFU/mg protein.
§75 U/ml recombinant human IL-6 were added every 48 h; specific activity $10^7$ CFU/mg protein.
°12.5 U/ml recombinant human GM-CSF were added every 48 h; specific activity $5 \times 10^7$ CFU/mg protein.

TABLE VIII

Differential Analysis of CD34+, DR−, CD71− Cells after Addition of Various Cytokines

| Cytokine | Day | Blasts | Pro | Myelo | MM | Band % | Seg | Eo | Baso | E | Mo |
|---|---|---|---|---|---|---|---|---|---|---|---|
| Control | 7 | 90 |  |  |  |  |  |  |  |  | 10 |
|  | 14 | 40 |  |  |  |  |  |  |  |  | 60 |
| IL-1α* | 7 | 82 |  |  |  |  |  |  |  |  | 18 |
| IL-6+ | 7 | 43 | 4 |  |  |  |  |  |  |  | 13 |
|  | 14 | 33 | 20 |  |  |  |  |  |  |  | 47 |
| GM-CSF§ | 7 | 39 | 33 |  | 9 | 5 | 6 |  | 5 |  | 2 |
|  | 14 | 18 | 5 |  | 42 | 3 | 12 |  | 20 |  |  |
|  | 21 | 4 |  | 1 | 66 | 9 | 7 |  |  |  | 4 |
|  | 28 | 2 |  |  | 61 | 3 | 1 | 8 |  |  | 24 |
|  | 35 | 14 |  |  | 18 | 8 | 8 | 9 |  |  | 52 |
|  | 42 |  |  |  |  |  |  |  |  |  | 100 |
| IL-3° | 7 | 52 | 40 |  | 1 | 2 | 2 |  | 2 | 1 |  |
|  | 14 | 29 | 26 |  | 26 | 2 | 3 |  | 14 |  |  |
|  | 21 | 13 | 4 | 2 | 28 | 2 | 3 |  | 48 |  |  |
|  | 28 | 14 | 3 |  | 35 | 5 | 1 |  | 35 |  | 7 |
|  | 35 | 9 |  |  | 20 | 7 | 6 |  | 27 |  | 31 |
|  | 42 | 2 |  |  | 5 | 4 |  | 16 | 2 | 71 |  |

TABLE VIII-continued

Differential Analysis of CD34+, DR⁻, CD71⁻ Cells after Addition of Various Cytokines

| Cytokine | Day | Blasts | Pro | Myelo | MM | Band % | Seg | Eo | Baso | E | Mo |
|---|---|---|---|---|---|---|---|---|---|---|---|
| IL-1α/ IL-3 | 7 | 48 | 42 | | 6 | 2 | 1 | | 2 | | |
| | 14 | 4 | 1 | 53 | 4 | 5 | | | 33 | | |
| | 21 | 3 | | | 44 | 1 | 1 | | 49 | | 2 |
| | 28 | 21 | 3 | | 34 | 4 | 3 | 1 | 27 | | 8 |
| | 35 | 3 | | | 23 | 4 | 29 | | 20 | | 21 |
| | 42 | 1 | | | 7 | 3 | 3 | | 16 | | 70 |
| | 56 | | | | | | 1 | | 8 | | 91 |

Differential cell counts were performed on Wright-Giesma stained cytocentrifuge preparations of cells removed from liquid culture. 200 Cells per sample were classified; if <200 cells appeared on a slide, all were classified. Abbreviations as in Table VII.
*2.5 U/ml recombinant human IL-1a were added every 48 h; specific activity $10^8$ CFU/mg protein.
+50 U/ml recombinant human IL-3 were added every 48 h; specific activity $10^8$ CFU/mg protein.
§75 U/ml recombinant human IL-6 were added every 48 h; specific activity $10^7$ CFU/mg protein.
°12.5 U/ml recombinant human GM-CSF were added every 48 h; specific activity $5 \times 10^7$ CFU/mg protein.

Example 2

Long-term bone marrow cultures (LTBMC) were initiated with $5 \times 10^3$ CD34⁺DR⁻CD15⁻ marrow cells/ml in plastic 35-mm tissue culture dishes containing 1 ml of Iscove's with 10% FBS and incubated at 37° C. in 100% humidified atmosphere containing 5% $CO_2$ in air. At this time, and every 48 h thereafter, cultures received nothing, or murine mast cell growth factor (MGF; c-kit ligand) alone or in combination with IL-3 or a GM-CSF/IL-3 fusion protein (FP; Broxmeyer, et al. Exp. Hematol. 18: 615, 1990). In cultures not receiving cytokines, viable cells were not detectable after two weeks while cultures receiving IL-3, FP, or MGF sustained hematopoiesis for 10 weeks. Addition of IL-3 or FP alone increased cell numbers by 100 fold by day 26, while the combination of MGF and FP expanded cell numbers 1000-fold ($5 \times 10^3$ cells at day 0; $12,500 \times 10^3$ at day 26). Over the 10 week period of LTBMAC, treatment with various cytokines led to the following cumulative increases over an input of 213 total assayable hematopoietic progenitor cells (HPC; CFU–GM+BFU–E+CFU–MK): IL-3, 868; FP, 1,265; MGF, 2,006; MGF+IL-3, 4,845; MGF+FP, 155,442. LTBMCs receiving MGF alone possessed a higher HPC cloning efficiency than those receiving IL-3 or FP and its addition increased the cloning efficiencies of cultures containing of IL-3 and FP. The presence of MGF did not increase the longevity of cultures receiving these cytokines.

TABLE IX

Total Cell Production of CD34₊, DR⁻, CD15⁻ Cells after Cytokine Addition

| | Day | |
|---|---|---|
| | 0 | 26 |
| Cytokine | Viable Cell count × $10^3$ | |
| None | 5 | 0 |
| *IL-3 | 5 | 140 |
| ⁺GM-CSF | 5 | 100 |
| °FP | 5 | 1400 |
| MGF | 5 | 520 |
| GM-CSF/IL-3 | 5 | 560 |
| MGF/ GM-CSF | 5 | 12,500 |
| MGF/IL-3 | 5 | 1,200 |
| MGF/FP | 5 | 10,000 |

Total cells/ml culture/1/2Yn = number of previous cell dilutions. Cultures were periodically split to allow for cellular expansion and to perform several analyses at different time points.
*500 pg/ml recombinant human IL-3 was added every 48 hours.
+200.0 pg/ml recombinant human GM-CSF was added every 48 hours.
°10.0 ng/ml of recombinant GM-CSF-IL-3 fusion protein was added each day.
100.0 ng/ml of murine recombinant mast cell growth factor (MGF) was added every 48 hours.

TABLE X

Differential Analysis of CD34+, DR⁻, CD15⁻Cells After Addition of Various Cytokines on Day 26 of Suspension Culture

| Cytokine | Blasts | Pro | Myelo | MM | Band | Seg | Lymph | Eo | Baso | Mo | Norm |
|---|---|---|---|---|---|---|---|---|---|---|---|
| FP | 3 | 7 | 9 | 9 | 27 | 3 | 5 | 2 | 9 | 0 | 5 |
| GM-CSF/ IL-3 | 1 | 7 | 4 | 13 | 24 | 32 | 4 | 3 | 4 | 0 | 0 |

TABLE X-continued

Differential Analysis of CD34+, DR⁻, CD15⁻Cells After Addition of Various Cytokines on Day 26 of Suspension Culture

| Cytokine | Blasts | Pro | Myelo | MM | Band | Seg | Lymph | Eo | Baso | Mo | Norm |
|---|---|---|---|---|---|---|---|---|---|---|---|
| MGF | 32 | 4 | 9 | 9 | 13 | 12 | 7 | 1 | 1 | 12 | 0 |
| MGF/GM-CSF | 21 | 10 | 15 | 12 | 14 | 7 | 5 | 2 | 3 | 11 | 0 |
| MGF/IL-3 | 38 | 3 | 15 | 12 | 13 | 4 | 2 | 2 | 4 | 7 | 2 |
| MGF/FP | 37 | 17 | 16 | 9 | 9 | 5 | 1 | 0 | 6 | 0 | 5 |

Differential cell counts were performed on Wright Giemsa stained cytocentrifuge preparations of cells removed from liquid culture. 200 cells per sample. Abbreviation used, Norm, normoblasts, other abbreviations as in Table VI. Cytokines were added at same dose as detailed in legend of Table I.

Example 3

Liquid culture systems supplemented with repeated 48-hourly cytokine additions were utilized to study cell populations cultured from two donors. Total cell production of CD34$^+$DR$^-$CD15$^-$ cells is shown in Table XI while assayable CFU-GM in these cultures over time is recorded in Table XIII. In the absence of exogenous cytokines, total cell numbers declined over a 1 to 2-week period and assayable CFU-GM persisted for only a 1 to 2-week period. In donor 1, MGF/FP cytokine combination promoted increased total cell production for 8 weeks, by which time cell numbers represented over 110×10$^3$ times the number present in the initial seeding populations. In donor 2 the same cytokine combination promoted increased total cell production for 6 weeks, by which time the cell numbers represented by over 16×10$^3$ times the number present in the initial seeding population. Assayable CFU-GM for donor 1 and donor 2 cultured with MGF/FP cytokine combination persisted for 6–8 weeks and 3–4 weeks, respectively and significantly surpassed the CFU-GM population initially assayable.

The cytokine combination MGF/IL-3 promoted over 2×10$^3$ fold increase in total cell production over the initial seeding for donor 1 at 6 weeks and donor 2 at 8 weeks. Additionally, viable cell counts remain high through 10 weeks. The assayable expansion of CFU-GM for donor 1 and 2 cultured with MGF/IL-3 cytokine combination persisted for 6–8 weeks for each donor and each significantly surpassed the CFU-GM population assayable initially.

Total BFU-E production by CD34$^+$DR$^-$CD15$^-$ cells is shown in Table XIV. In donor 1 and donor 2 the cytokine combination MGF/FP persisted for 1–2 weeks and 3–4 weeks, respectively with only donor 2 showing a significant increase over the BFU-E population initially assayable. The cytokine combination MGF/IL-3 persisted in donor 1 for 2–3 weeks and in donor 2 for 3–4 weeks, with both showing significant increase in weeks 1–2 over the BFU-E population initially assayable.

Total CFU-MK production by CD34+DR$^-$CD15$^-$ cells is shown in Table XV. The cytokine combination of MGF/IL-3 for both donors 1 and 2 show CFU-MK persistence for through 10 weeks and each has significantly surpassed the initially assayable CFU-MK population. Donors 1 and 2 show CFU-MK persistence for 6–8 weeks and 8–10 weeks, respectively, both showing significant increases over the initial CFU-MK population.

Morphological analysis of the cells in the suspension cultures of donor 1 during the period of observation revealed changes in the cellular composition of the population following the addition of various cytokines, see Table XII, which shows the differential analysis of CD34$^+$DR$^-$CD15$^-$ cells. Cultures receiving MGF/FP were composed of 11% blasts by 14 days and cultures receiving MGF/IL-3 were composed of 17% blasts by 14 days. The highest percentage of blasts by 14 days was in the cultures receiving MGF alone which were composed of 30% blasts. In contrast IL-3 and FP containing cultures had reduced the percentage of blasts cells appreciably by day 14.

Table XVI depicts the percentage of total cells which give rise to progenitor cells of colony forming units. Although MGF percentages are high the overall expansion of cultures receiving MGF is not as substantial, however the cultures receiving MGF/IL-3 cytokines provide high plating percentages and substantial overall expansion (see Tables XI–XV).

TABLE XI

Total Cell Production of CD34,DR⁻CD15⁻ Cells Cultured in the Presence of Various Cytokines
viable cell count × 10$^3$/ml

| | Week | | | | | | |
|---|---|---|---|---|---|---|---|
| Cytokine | 1 | 2 | 3 | 4 | 6 | 8 | 10 |
| Donor 1 | | | | | | | |
| None | 1 | 0 | 0 | 0 | 0 | 0 | 0 |
| IL-3[1] | 28 | 144 | 271 | 560 | 480 | 762 | 960 |
| GM-CSF[2] | 12 | 107 | 436 | 1,085 | 2,680 | 2,080 | 1,760 |
| IL-3/GM-CSF | 23 | 244 | 742 | 1,620 | 1,979 | 2,035 | 2,720 |
| FP[3] | 42 | 262 | 587 | 1,240 | 3,000 | 1,494 | 480 |
| MGF[4] | 8 | 104 | 933 | N.D.[5] | 1,680 | 1,760 | 640 |
| MGF/FP | 101 | 1,211 | 35,100 | 101,000 | 262,400 | 550,000 | 100,000 |
| MGF/IL-3 | 38 | 213 | 978 | 2,820 | 10,800 | 5,680 | 5,120 |
| Donor 2 | | | | | | | |
| None | 1 | 0 | 0 | 0 | 0 | 0 | 0 |
| IL-3 | 24 | 180 | 650 | 605 | 1,400 | 960 | 864 |
| FP | 41 | 810 | 2,100 | 6,680 | 1,840 | 4,320 | 5,280 |
| MGF | 8 | 27 | 71 | 98 | 230 | 70 | 0 |
| MGF/FP | 100 | 1,280 | 15,700 | 6,400 | 81,000 | 19,520 | 0 |
| MGF/IL-3 | 36 | 305 | 780 | 1,380 | 6,960 | 10,400 | 5,440 |
| Donor 3 | | | | | | | |
| MGF/FP | N.D. | 5,040 | 14,400 | 14,800 | 8,960 | | |

Total cells - cells/ml culture/(2)$^n$ where n = number of previous demidepopulations.
Cultures were seeded at 5 × 10$^3$ cells/ml.
[1]500 pg/ml recombinant human IL-3 was added every 48 hours; specific activity 3.5 × 10$^8$ CFU/mg protein.
[2]250 pg/ml recombinant human GM-CSF was added every 48 hours; specific activity 2 × 10$^8$ protein.

TABLE XI-continued

Total Cell Production of CD34+DR−CD15− Cells Cultured in the Presence of Various Cytokines
viable cell count × 10³/ml

| Cytokine | Week 1 | 2 | 3 | 4 | 6 | 8 | 10 |
|---|---|---|---|---|---|---|---|

[3] 10 ng/ml recombinant human FP was added every 48 hours; specific activity 1–2 × 10⁸ CFU/mg protein.
[4] 50 ng/ml recombinant murine MGF was added every 48 hours; specific activity 10⁶ CFU/mg protein.
[5] N.D. = not determined.

TABLE XII

Differential Analysis of CD34+DR−CD15− Cells Following Culture with Various Cytokines

| Cytokine | Day | Blast % | Pro | Myelo | Meta | Band | Seg | Baso | Eos | Mono |
|---|---|---|---|---|---|---|---|---|---|---|
| Post Sort | 0 | 82 | 1 | 1 | | | | 6 | | 10 |
| IL-3[1] | 7 | 10 | 8 | 16 | 2 | | 9 | 50 | 2 | 3 |
| | 14 | 2 | 4 | 39 | 4 | 3 | 10 | 28 | | 10 |
| | 28 | 3 | 6 | 13 | 3 | 1 | 6 | 61 | | 7 |
| FP[2] | 7 | 10 | 21 | 52 | 5 | | 2 | 7 | | 3 |
| | 14 | 1 | 4 | 17 | 8 | 3 | 20 | 14 | | 33 |
| | 28 | | 1 | 24 | 7 | 4 | 36 | 8 | | 20 |
| MGF[3] | 7 | 54 | 39 | 3 | | | | 1 | | 3 |
| | 14 | 30 | 38 | 9 | 1 | 1 | 1 | | | 20 |
| | 28 | 1 | 7 | 21 | 18 | 13 | 15 | 1 | 1 | 23 |
| MGF/FP | 7 | 29 | 22 | 23 | 3 | | 4 | 18 | | 1 |
| | 14 | 11 | 22 | 16 | 4 | 2 | 4 | 13 | | 28 |
| | 28 | 1 | 8 | 13 | 12 | 2 | 10 | 2 | | 52 |
| MGF/IL-3 | 7 | 31 | 15 | 48 | | | 2 | 4 | | |
| | 14 | 17 | 14 | 9 | 2 | 4 | 8 | 34 | | 12 |
| | 28 | | 8 | 46 | 17 | 2 | 17 | 2 | | 8 |

Differential cell counts were performed on Wright-Giemsa-stained cytocentrifuge preparations of cells removed from liquid culture. ≧100 cells per sample were classified. Abbreviations: Pro, promyelocyte; Myelo, myelocyte; Meta, metamyelocyte; Band, neutrophil band form; Seg, segmented neutrophil; Baso, basophil; Eos, eosinophil; Mono, monocyte.
[1] 500 pg/ml recombinant human IL-3, specific activity 3.5 × 10⁸ CFU/mg protein.
[2] 10 ng/ml recombinant human FP, specific activity 1–2 × 10⁸ CFU/mg protein.
[3] 50 ng/ml recombinant murine MGF, specific activity 10⁶ CFU/mg protein.

TABLE XIII

Total CFU-GM Production by CD34+DR−CD15− Cells Cultured in the Presence of Various Cytokines
CFU-GM/ml culture[1]

| Cytokine | Week 1 | 2 | 3 | 4 | 6 | 8 |
|---|---|---|---|---|---|---|
| Donor 1 | | | | | | |
| None | 8 | 0 | 0 | 0 | 0 | 0 |
| IL-3[2] | 132 | 28 | 80 | N.D.[5] | N.D. | 128 |
| GM-CSF[3] | 192 | 112 | 88 | N.D. | 128 | 0 |
| IL-3/GM-CSF | 196 | 104 | 36 | N.D. | 128 | 576 |
| FP[4] | 86 | 112 | 128 | 176 | N.D. | 64 |
| MGF[5] | 290 | 396 | 608 | 448 | 96 | 0 |
| MGF/FP | 376 | 1,600 | 14,800 | 58,000 | 80,000 | 0 |
| MGF/IL-3 | 144 | 348 | 104 | 416 | 2,528 | 192 |
| Donor 2 | | | | | | |
| None | 0 | 0 | 0 | 0 | 0 | N.D. |
| IL-3 | 232 | 196 | 96 | 16 | 64 | N.D. |
| FP | 84 | 148 | 288 | 320 | 544 | N.D. |
| MGF | 106 | 152 | 360 | 64 | 128 | N.D. |
| MGF/FP | 114 | 1,440 | 10,600 | N.D. | N.D. | N.D. |
| MGF/IL-3 | 62 | 240 | 504 | 32 | 1,024 | N.D. |
| Donor 3 | | | | | | |
| MGF/FP | N.D. | 12,448 | 32,936 | 32,264 | 1,254 | 0 |

Total CFU-GM = CFU-GM/ml culture/(2)ⁿ where n = number of previous demidepopulations.
[1] Cultures were seeded at 5 × 10³ cells/ml. CFU-GM/5 × 10³ cells in initial population: Donor 1, 150; Donor 2, 227; Donor 3, 144. Colonies grown in methylcellulose containing 500 pg/ml GM-CSF and 1 U human urinary erythropoietin and enumerated after 14 days.
[2] 500 pg/ml recombinant human IL-3 was added every 48 hours; specific activity 3.5 × 10⁸ CFU/mg protein.
[3] 250 pg/ml recombinant human GM-CSF was added every 48 hours; specific activity 2 × 10⁸ CFU/mg protein.
[4] 10 ng/ml recombinant human FP was added every 48 hours; specific activity 1–2 × 10⁸ CFU/mg protein.
[5] 50 ng/ml recombinant murine MGF was added every 48 hours; specific activity 10⁶ CFU/mg protein.
[6] N.D. - not determined.

TABLE XIV

Total BFU-E Production by CD34+DR−CD15− Cells Cultured in the Presence of Various Cytokines
BFU-E/ml culture[1]

| Cytokine | WEEK | | | |
|---|---|---|---|---|
| | 1 | 2 | 3 | 4 |
| Donor 1 | | | | |
| None | 0 | — | — | — |
| IL-3 | 24 | 0 | 0 | 0 |
| GM-CSF | 8 | 0 | 0 | 0 |
| IL-3/GM-CSF | 22 | 4 | 0 | 0 |
| FP | 20 | 4 | 0 | 0 |
| MGF | 8 | 40 | 0 | 0 |
| MGF/FP | 98 | 0 | 0 | 0 |
| MGF/IL-3 | 238 | 4 | 0 | 0 |
| Donor 2 | | | | |
| Control | 0 | — | — | — |
| IL-3 | 40 | 28 | 0 | 0 |
| FP | 132 | 68 | 56 | 16 |
| MGF | 6 | 0 | 0 | 0 |
| MGF/FP | 662 | 100 | 200 | 0 |
| MGF/IL-3 | 1,062 | 272 | 40 | 0 |

Total BFU-E = BFU-E/ml culture/$(2)^n$ where number of previous demidepopulations.
[1]Cultures were seeded at 5 × $10^3$ cells/ml. Each point represents the mean of two separate experiments. Mean BFU-E/5 × $10^3$ cells in initial population: = Donor 1, 173; Donor 2, 154. Colonies grown in methylcellulose containing 500 pg/ml GM-CSF and 1 U human urinary erythropoietin and enumerated after 12 days.
[2]500 pg/ml recombinant human IL-3 was added every 48 hours; specific activity 3.5 × $10^8$ CFU/mg protein.
[3]250 pg/ml recombinant human GM-CSF was added every 48 hours; specific activity 2 × $10^8$ CFU/mg protein.
[4]10 ng/ml recombinant human FP was added every 48 hours; specific activity 1–2 × $10^3$ CFU/mg protein.
[5]50 ng/ml recombinant murine MGF was added every 48 hours; specific activity $10^6$ CFU/mg protein.

TABLE XV

Total CFU-MK Production by CD34+DR−CD15− Cells Cultured in the Presence of Various Cytokines
CFU-MK/ml culture[1]

| Cytokine | Week | | | | | |
|---|---|---|---|---|---|---|
| | 2 | 3 | 4 | 6 | 8 | 10 |
| Donor 1 | | | | | | |
| None | 0 | 0 | 0 | 0 | 0 | 0 |
| IL-3[2] | 14 | 74 | 100 | 118 | 48 | N.D.[5] |
| GM-CSF[3] | 12 | 40 | 20 | 48 | 32 | 0 |
| IL-3/GM-CSF | 20 | 80 | 96 | 120 | N.D. | N.D. |
| FP[4] | 28 | 120 | 184 | 118 | 96 | 64 |
| MGF[5] | 6 | 12 | 36 | 20 | 0 | 0 |
| MGF/FP | 40 | 120 | 120 | 120 | N.D. | 0 |
| MGF/IL-3 | 26 | 90 | 208 | 220 | 128 | 64 |
| Donor 2 | | | | | | |
| None | 8 | 0 | 0 | 0 | 0 | 0 |
| IL-3 | 26 | 100 | 140 | 140 | 64 | 64 |
| GM-CSF | 24 | 40 | 60 | 80 | 32 | 0 |
| IL-3/GM-CSF | 40 | 120 | 160 | 200 | 64 | 64 |
| FP | 56 | 120 | 200 | 200 | 96 | 64 |
| MGF | 10 | 36 | 60 | 60 | 0 | 0 |
| MGF/FP | 56 | 200 | 200 | 200 | 40 | 0 |
| MGF/IL-3 | 34 | 120 | 240 | 260 | 160 | 192 |

Total CFU-MK = CFU-MK/ml culture/$(\frac{1}{2})^n$ where n = number of previous demidepopulations.
[1]Cultures were seeded at 5 × $10^3$ cells/ml. Each point represents the mean of two separate experiments. Mean CFU-MK/5 × $10^3$ cells in initial populations = 0. Colonies cultured in fibrin clot containing 1 ng IL-3 and enumerated 15 days.
[2]1 ng/ml recombinant human IL-3 was added every 48 hours; specific activity 3.5 × $10^8$ CFU/mg protein.
[3]200 pg/ml recombinant human GM-CSF was added every 48 hours; specific activity 2 × $10^8$ CFU/mg protein.
[4]10 ng/ml recombinant human FP was added every 48 hours; specific activity 1–2 × $10^8$ CFU/mg protein.
[5]100 ng/ml recombinant murine MGF was added every 48 hours; specific activity $10^8$ CFU/mg protein.
[6]N.D. - not determined.

TABLE XVI

Plating Efficiency of CD34+DR−CD15− Cells Cultured in the Presence of Various Cytokines

| Cytokine | Week | | | | | |
|---|---|---|---|---|---|---|
| | 1 | 2 | 3 | 4 | 6 | 8 |
| | % Plating Efficiency[1] | | | | | |
| None | N.D.[6] | — | — | — | — | — |
| IL-3[2] | 0.86 | 0.072 | 0.023 | 0.003 | 0.005 | 0.009 |
| GM-CSF[3] | 1.67 | 0.105 | 0.020 | N.D. | 0.005 | 0.000 |
| IL-3/GM-CSF | 0.96 | 0.044 | 0.005 | N.D. | 0.006 | 0.028 |
| FP[4] | 0.42 | 0.039 | 0.019 | 0.010 | 0.015 | 0.002 |
| MGF[5] | 2.58 | 0.493 | 0.580 | 0.065 | 0.031 | 0.000 |
| MGF/FP | 0.65 | 0.127 | 0.056 | 0.029 | 0.015 | 0.000 |
| MGF/IL-3 | 2.10 | 0.173 | 0.041 | 0.008 | 0.019 | 0.002 |

[1]% Plating Efficiency = colonies enumerated/cells cultured × 100%. Cells at each timepoint were counted and cultured in methylcellulose containing 500 pg GM-CSF and 1 U human urinary erythropoietin or in fibrin clot containing 1 ng IL-3 and enumerated at 14 days. Each point represents the mean of two to four separate experiments. Mean cloning efficiency of initial (day 0) population: 4.54%.
[2]500 pg/ml recombinant human IL-3 was added every 48 hours; specific activity 3.5 × $10^8$ CFU/mg protein.
[3]200 pg/ml recombinant human GM-CSF was added every 48 hours; specific activity 2 × $10^8$ CFU/mg protein.
[4]10 ng/ml recombinant human FP was added every 48 hours; specific activity 1–2 × $10^8$ CFU/mg protein.
[5]100 ng/ml recombinant murine MGF was added every 48 hours; specific activity $10^8$ CFU/mg protein.
[6]N.D. - not determined.

Example 4

Serum-free long-term suspension human bone marrow culture system. Serum free liquid culture system media was prepared as described by Ponting, et al. (1991) Growth Factors 4:165–173. Both serum frees and serum containing cultures were initiated with CD34+DR− CD15− cells, and supplemented every 48 hours with c-kit ligand (MGF) and a GM-CSF/IL-3 fusion protein (FP).

As shown in Table XVII, cultures maintained in serum-free media were characterized by far less total cell production than has been observed in comparable serum containing cultures. Over six weeks of observation, these cultures only increased total cell number by 24-fold. However, the progenitor cell cloning efficiency in serum-free cultures was 1.4% after 28 days of LTBMC, in comparison to a cloning efficiency of 0.03% in comparable serum-containing cultures. These studies suggest that the serum-free culture system is preferable for expanding progenitor cell numbers at the expense of impairing the production of more differentiated cells.

TABLE XVII

Plating Efficiency of CD34$^+$ DR$^-$ CD15$^-$ Cells Cultured in Serum-Free Medium*

| Days in Culture | Cell no. × 10$^3$ | Progenitor Cells | |
|---|---|---|---|
| | | CFU-GM | HPP-CFC |
| 0 | 10 | 375 | 40 |
| 14 | 30 | 744 | 9 |
| 28 | 70 | 1,050 | 21 |
| 42 | 140 | 140 | 42 |

*CD34$^+$ DR$^-$ CD15$^-$ cells were suspended in serum-free medium and supplemented with 100 ng/ml of c-kit ligand (MGF) and 10 ng/ml of FP every 48 hours.

It is evident from the above results, that substantial cell expansions may be obtained from hematopoietic progentor cells in the substantial or complete absence of stromal cells. These cultures may be grown and maintained for extended periods of time, where progenitor cells are able to expand and maintain the culture. Disadvantages associated with the presence of stromal cells, the lack of a controlled system dependent upon the nature and activity of the stromal cells, is avoided by using factors individually or in combination. In this manner, substantial expansions of hematopoietic cells from a limited number of progenitors can be achieved in a controlled substantially reproducible manner.

All publications and patent applications cited in this specification are herein incorporated by reference as if each individual publication or patent application were specially and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for autologous hematopoietic cell transplantation in a patient receiving cytoreductive therapy, comprising:
   a. removing hematopoietic progenitor cells from the patient prior to cytoreductive therapy;
   b. expanding the hematopoietic progenitor cells ex vivo with
      (1) a growth factor comprising a GM-CSF/IL-3 fusion protein, and
      (2) mast cell growth factor (steel factor); to provide a cellular preparation comprising an expanded population of hematopoietic progenitor cells; and
   c. administering the cellular preparation to the patient following cytoreductive therapy.

* * * * *